US008563605B2

(12) United States Patent
Miyanari et al.

(10) Patent No.: US 8,563,605 B2
(45) Date of Patent: Oct. 22, 2013

(54) THERAPEUTIC AGENT FOR MALE STERILITY

(75) Inventors: Setsuko Miyanari, Tokyo (JP); Masumi Takahashi, Tokyo (JP); Masahiro Ishizuka, Tokyo (JP); Tohru Tanaka, Tokyo (JP)

(73) Assignee: SBI Pharmaceuticals Co., Ltd., Tokyo (JP)

( * ) Notice: Subject to any disclaimer, the term of this patent is extended or adjusted under 35 U.S.C. 154(b) by 86 days.

(21) Appl. No.: 12/736,782

(22) PCT Filed: May 13, 2009

(86) PCT No.: PCT/JP2009/002086

§ 371 (c)(1), (2), (4) Date: Nov. 9, 2010

(87) PCT Pub. No.: WO2009/139156

PCT Pub. Date: Nov. 19, 2009

(65) Prior Publication Data

US 2011/0065787 A1 Mar. 17, 2011

(30) Foreign Application Priority Data

May 14, 2008 (JP) ................................ 2008-126610

(51) Int. Cl.
*A01N 55/02* (2006.01)
*A61K 31/295* (2006.01)

(52) U.S. Cl.
USPC .......................................... 514/502; 514/561

(58) Field of Classification Search
None
See application file for complete search history.

(56) References Cited

U.S. PATENT DOCUMENTS

| | | | | |
|---|---|---|---|---|
| 6,469,012 | B1 | 10/2002 | Ellis et al. | |
| 2004/0234555 | A1 | 11/2004 | Oshida et al. | |
| 2007/0249721 | A1 | 10/2007 | Ito | |
| 2008/0026075 | A1 * | 1/2008 | Kondo et al. ................ | 424/630 |

FOREIGN PATENT DOCUMENTS

| | | | |
|---|---|---|---|
| CN | 1942163 | A | 4/2007 |
| JP | 2003-040770 | A | 2/2003 |
| WO | WO 2006/025286 | A1 | 3/2006 |
| WO | WO 2007110977 | A1 * | 10/2007 |
| WO | WO 2007/126653 | A2 | 11/2007 |

OTHER PUBLICATIONS

Suleiman et al, Lipid Peroxidation and Human Sperm Motility Protective Role of Vitamin E, J. Androl. 1996:17:530-537.*

Agarwal et al, Review, Reproductive Biomedicine Online, vol. 8, No. 6, 2004, pp. 616-627.*

Ferromia product, by Eisai Co. Ltd, Jul. 2009 (10th version).*

International Search Report mailed Jun. 16, 2009, in PCT/JP2009/002086, 2 pages.

Kato et al., "Lipid Peroxidation in Boar Spermatozoa," Japanese Journal of Animal Al Research, Sep. 1983, 5(3):72-76, with English translation, 9 pages.

Telišman et al., "Semen Quality and Reproductive Endocrine Function in Relation to Biomarkers of Lead, Cadmium, Zinc, and Copper in Men," Environ. Health Perspect., Jan. 2000, 108(1):45-53.

Telišman et al., "Reproductive toxicity of low-level lead exposure in men," Environmental Research, 2007, 105(2):256-266.

Arnold et al., "Mutagenicity studies with δ-aminolaevulinic acid," Ed. Cosmet. Toxicol., 1975, 13:63-68.

Kasperczyk et al., "Assessment of semen function and lipid peroxidation among lead exposed men," Toxicology and Applied Pharmacology, 2008, 228:378-384.

* cited by examiner

*Primary Examiner* — Brandon Fetterolf
*Assistant Examiner* — Jean Cornet
(74) *Attorney, Agent, or Firm* — Foley & Lardner LLP

(57) ABSTRACT

The present invention is intended to provide an agent for treating male infertility which is highly effective to male infertility, and having few side effects. To achieve the object, an agent for treating male infertility comprising δ-amino levulinic acid shown by general formula (1), its derivative or salt thereof:

$$R^2R^1NCH_2COCH_2CH_2COR^3 \quad (1)$$

[wherein $R^1$ and $R^2$ independently represent a hydrogen atom, alkyl group, acyl group, alkoxycarbonyl group, aryl group, or aralkyl group; $R^3$ represents a hydroxy group, alkoxy group, acyloxy group, alkoxycarbonyloxy group, aryloxy group, aralkyloxy group or amino group] can be used.

6 Claims, 1 Drawing Sheet

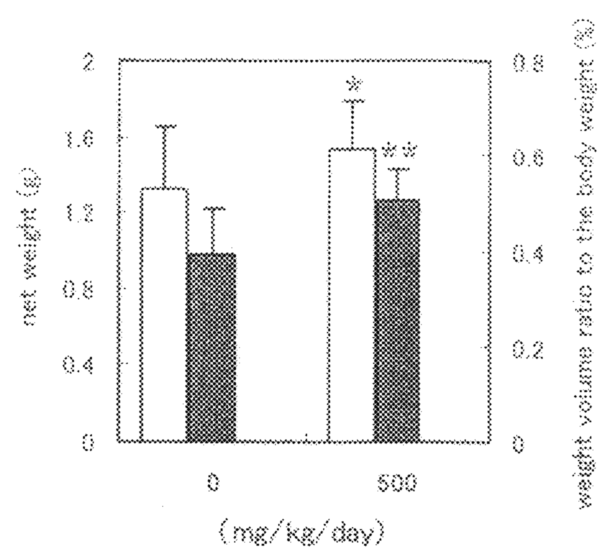
*: P<0.05 **: P<0.01

THERAPEUTIC AGENT FOR MALE STERILITY

TECHNICAL FIELD

The present invention relates to a novel agent for treating male infertility.

BACKGROUND ART

Causes of male infertility are wide-ranging, and many cases are involved with various factors associated in a complex manner. Generally, spermatogenic dysfunction, obstruction of sperm transport, sperm dysfunction and sexual dysfunction are thought to be the four major reasons of male infertility. Among them, in spermatogenic dysfunction and sperm dysfunction, there exists oligozoospermia and asthenospermia exhibiting symptoms wherein sperm motility is lowered, or wherein sperm concentration or number of sperms is decreased. Further, unexplained sudden spermatogenic dysfunction is observed frequently as male infertility.

Sexual dysfunction is so-called erectile dysfunction, and it is reported to represent 15% of male infertility. Erection is attained when smooth muscle of corpus cavernosum penis is relaxed, blood flow from deep artery of penis is increased, and vein is compressed by the expansion of tissues at the same time, and thus blood flow is restricted. First, nitric oxide synthesized by nitric oxide (NO) synthetase in endothelia cells is diffused in smooth muscle cells in the corpus cavernosum penis. Next, NO binds with the heme of guanylate cyclase to activate the enzyme, and cyclic guanosine monophosphate (cGMP) is synthesized from guanosine triphosphate. As cGMP decreases calcium concentration in smooth muscle cells, relaxation of smooth muscles progresses with the increase of cGMP concentration, and the blood flow of penile artery increases.

Conventionally, hormone treatment and nonendocrine treatment were performed as treatment of male infertility. Specific examples include administration of hormonal agent such asgonadotropin and estrogen; and administration of nonendocrine agents including protease, adenosine 5'-triphosphate (ATP), coenzyme Q10, vitamins such as vitamin B12 and folic acid, antioxidant agents such as vitamin E and vitamin C, trace elements such as zinc and selenium, L-carnitine and herbal medicine. However, since these agents do not act specifically on germ cells or germ tissues, it cannot be said that they exert a significant effect.

Further, sildenafil citrate (hereinafter abbreviated as “sildenafil”) (see patent document 1) is manufactured and authorized by FDA as an agent for treating erectile dysfunction. Sildenafil exhibits an effect by inhibiting selectively an enzyme that metabolizes cGMP to non-activated 5'-cGMP.

However, it had drawbacks in that it is possible to induce rapid and significant decrease of blood pressure, or to induce angina impairing oxygen supply to heart as side effects. Moreover, it is said that the effectiveness is as low as about 50%.

PRIOR ART DOCUMENTS

Patent Documents

Patent document 1: U.S. Pat. No. 6,469,012

SUMMARY OF THE INVENTION

Object to be Solved by the Invention

The present invention is intended to provide an agent for treating male infertility with high effectiveness to male infertility, and with few side effects.

Means to Solve the Object

The present inventors made a keen study in view of such circumstances, and found out that the administration of δ-amino levulinic acid, its derivative or salt thereof, exhibits an excellent therapeutic effect to male infertility, particularly to male infertility caused by oligozoospermia and asthenospermia, or to male infertility caused by erectile dysfunction. The present invention has been thus completed.

Specifically, the present invention provides an agent for treating male infertility comprising δ-amino levulinic acid shown by general formula (1), its derivative, or salt thereof as an active ingredient.

$$R^2R^1NCH_2COCH_2CH_2COR^3 \quad (1)$$

[wherein $R^1$ and $R^2$ independently represent a hydrogen atom, alkyl group, acyl group, alkoxycarbonyl group, aryl group or aralkyl group; $R^3$ represents a hydroxy group, alkoxy group, acyloxy group, alkoxycarbonyloxy group, aryloxy group, aralkyloxy group or amino group]

Effect of the Invention

The agent for treating male infertility of the present invention exhibits an excellent therapeutic effect to male infertility, and is particularly useful to male infertility caused by oligozoospermia and asthenospermia, or male infertility caused by erectile dysfunction.

BRIEF DESCRIPTION OF DRAWINGS

FIG. 1 It is a FIGURE showing the weight change of rat seminal vesicle when ALA is administered.

DESCRIPTION OF EMBODIMENTS

The active ingredient of the agent for treating male infertility of the present invention is δ-amino levulinic acid represented by the above general formula (1), its derivative, or salt thereof. The δ-amino levulinic acids are known to be useful as photosensitizing agents in photodynamic therapy (Published Japanese Translation of PCT International Publication No. 2004-505105), agent for promoting swine growth (Japanese Laid-Open Patent Application No. 2003-40770), agent for improving immune function (Japanese Laid-Open Patent Application No. 2006-96746), etc. However, effect on male infertility has not been known at all.

As alkyl group represented by $R^1$ and $R^2$ in the general formula (1), a linear or branched alkyl group with 1 to 24 carbons is preferred, and an alkyl group with 1 to 18 carbons is more preferred, and an alkyl group with 1 to 6 carbons is particularly preferred. Examples of alkyl group with 1 to 6 carbons include methyl group, ethyl group, n-propyl group, isopropyl group, n-butyl group and sec-butyl group, etc.

As acyl group, a linear or branched alkanoyl group, alkenylcarbonyl group or aroyl group with 1 to 12 carbons is preferred, and an alkanoyl group with 1 to 6 carbons is particularly preferred. Examples of the acyl group include an formyl group, acetyl group, propionyl group and butyryl group, etc.

As alkoxycarbonyl group, an alkoxycarbonyl group with total carbons of 2 to 13 is preferred, and an alkoxycarbonyl group with 2 to 7 carbons is particularly preferred. Examples of the alkoxycarbonyl group include methoxycarbonyl group, ethoxycarbonyl group, n-propoxycarbonyl group and isopropoxycarbonyl group, etc.

As aryl group, an aryl group with 6 to 16 carbons is preferred, and examples include phenyl group and naphtyl group, etc.

As aralkyl group, a group consisting of an aryl group with 6 to 16 carbons, and the above alkyl group with 1 to 6 carbons is preferred, and examples include benzyl group, etc.

As alkoxy group represented by $R^3$, a linear or branched alkoxy group with 1 to 24 carbons is preferred, and an alkoxy group with 1 to 16 carbons is more preferred, and an alkoxy group with 1 to 12 carbons is particularly preferred. Examples of the alkoxy group include methoxy group, ethoxy group, n-propoxy group, isopropoxy group, n-butoxy group, pentyloxy group, hexyloxy group, octyloxy group, decyloxy group and dodecyloxy group, etc.

As acyloxy group, a linear or branched alkanoyloxy group with 1 to 12 carbons is preferred, and an alkanoyloxy group with 1 to 6 carbons is particularly preferred. Examples of the acyloxy group include an acetoxy group, propionyloxy group and butyryloxy group, etc.

As alkoxycarbonyloxy group, an alkoxycarbonyloxy group with total carbons of 2 to 13 is preferred, and an alkoxycarbonyloxy group with total carbons of 2 to 7 is particularly preferred. Examples of the alkoxycarbonyloxy group include a methoxycarbonyloxy group, ethoxycarbonyloxy group, n-propoxycarbonyloxy group and isopropoxycarbonyloxy group, etc.

As aryloxy group, an aryloxy group with 6 to 16 carbons is preferred, and examples include phenoxy group and naphtyloxy group, etc. As aralkyloxy group, a group having the above aralkyl group is preferred, and examples include benzyloxy group, etc.

In the general formula (1), as $R^1$ and $R^2$, a hydrogen atom is preferred. As $R^3$, a hydroxy group, alkoxy group or aralkyloxy group is preferred, and a hydroxy group or alkoxy group with 1 to 0.12 carbons is more preferred. A methoxy group or hexyloxy group is particularly preferred.

Examples of δ-amino levulinic acid derivatives include ester derivatives such as δ-amino levulinic acid methyl ester, δ-amino levulinic acid ethyl ester, δ-amino levulinic acid propyl ester, δ-amino levulinic acid butyl ester, δ-amino levulinic acid pentyl ester and δ-amino levulinic acid hexyl ester. Particularly, δ-amino levulinic acid methyl ester or δ-amino levulinic acid hexyl ester is preferred.

Salts of δ-amino levulinic acid or its derivative are not particularly limited, while a pharmaceutically acceptable acid addition salt of an inorganic acid or organic acid is preferred. Examples of acid addition salt of an inorganic acid include hydrochloride, hydrobromate, hydrosulfate, nitrate and phosphate. Examples of acid addition salt of an organic acid include acetate, lactate, citrate, tartrate, succinate, maleate, fumarate and ascorbate. Particularly, δ-amino levulinic acid hydrochloride or δ-amino levulinic acid phosphate is preferred.

These salts can be manufactured by chemical synthesis or by a method using microorganisms or enzyme. Examples of these methods include methods described in Japanese Laid-Open Patent Application No. 4-9360, Published Japanese Translation of PCT International Publication No. 11-501914, Japanese Laid-Open Patent Application No. 2006-182753, Japanese Laid-Open Patent Application No. 2005-314361, and Japanese Laid-Open Patent Application No. 2005-314360.

As it is described in the following examples, δ-amino levulinic acid, its derivative or salt thereof have an effect to increase seminal vesicle weight, and to ameliorate erectile dysfunction. Therefore, the δ-amino levulinic acid, its derivative or salt thereof are useful for treating male infertility, particularly oligozoospermia and asthenospermia, or erectile dysfunction.

Further, the agent for treating male infertility of the present invention is preferred to comprise a combination of δ-amino levulinic acid, its derivative or salt thereof, with an iron compound in order to enhance its therapeutic effect.

Herein, the iron compound is not particularly limited as long as it is a compound comprising iron in its molecule. Examples include ferric chloride, iron sesguioxide, sodium iron chlorophyllin, ferritin iron, ferrous citrate, iron sodium citrate, iron ammonium citrate, ferrous fumarate, ferrous pyrophosphate, ferric pyrophosphate, saccharated iron oxide, iron acetate, iron oxalate, ferrous succinate, iron sodium succinate citrate, herne iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate, iron choline citrate, ferrous formate, ferric formate, ferric ammonium potassium oxalate, ferrous sulfate, ferric sulfate, iron ammonium sulfate, ferric carbonate, ferrous chloride, ferric chloride, andiron oxide, etc. These compounds may be used alone or by combining 2 or more of these. As iron compounds, ferrous citrate, ferrous fumarate, ferric pyrophosphate, saccharated iron oxide and iron dextran used commonly for medical use are particularly preferred.

In the present invention, the combination ratio of δ-amino levulinic acid, its derivative or salt thereof to iron compound is preferably 1:0.125 to 1:4 as mass ratio, and particularly preferably 1:0.25 to 1:1.

The agent for treating male infertility of the present invention may be prepared by common methods by mixing a pharmaceutically acceptable carrier, for example, an excipient, binding agent, disintegrant, lubricant, coloring agent, flavoring agent, and coating agent according to need to the above components.

Dosage forms are not particularly limited, and can be appropriately selected according to the therapeutic purpose. Examples include formulation for oral administration such as granules, fine grain agent and tablets; formulation for injection such as liquid agent and powder formulation dissolved before use; formulation for transdermal administration such as ointment, liquid agent, cream and gel; and formulation for parental administration such as suppository. Methods for administrating these formulations include oral administration, intravenous administration, intramuscular administration, local administration to affected area, intraperitoneal administration, transdermal administration, and intrarectal administration. Among these, oral administration, intraperitoneal administration, local administration to affected area, and intravenous administration are preferred.

In the present invention, when δ-amino levulinic acid, its derivative, or salt thereof is used in combination with an iron compound, they may be administered at the same time, or they may be administered separately with a time interval. Specifically, δ-amino levulinic acid, its derivative or salt thereof and the iron compound may be formulated as a single formulation, or may be used as a set (kit) by being formulated separately. When they are formulated separately, they may have a different dosage form. Further, the administration frequency of each component may be different.

In the present invention, the dosage amount of δ-amino levulinic acid, its derivative or salt thereof, depends on the administration method, symptoms and body weight of the patient, or tumor types. For example, in case of oral administration, the dosage is 0.001 mg to 10 g per 1 kg of body weight at one time, preferably 0.01 mg to 5 g, more preferably 0.1 to 1000 mg, and particularly preferably 1 to 600 mg per 1 kg of body weight. Further, the dosage amount of iron compound depends on the administration method, symptoms and body weight of the patient, or tumor types. For example, in case of oral administration, the dosage is 0.001 mg to 10 g per 1 kg of body weight at one time, preferably 0.01 to 1000 mg, and particularly preferably 0.1 to 500 mg per 1 kg of body weight.

The timing to administer the agent for treating male infertility of the present invention is not particularly limited as long as, it is administered before performing sexual intercourse, and it is preferred to administer the agent between 90 days before sexual intercourse and the day of sexual intercourse, more preferably between 30 days before and the day of sexual intercourse, and particularly preferably between 10 days before and the day of sexual intercourse. The number of times of administration may be once a day, but may be administered several times a day, not being limited to once a day. When administering the agent for several days, it may be administered continuously or non-continuously during the above period.

The diseases being the subject for applying the agent for treating male infertility of the present invention is male infertility in general, and it is particularly preferred to apply the agent to male infertility caused by oligozoospermia and asthenospermia, or to male infertility caused by erectile dysfunction. Further, the agent for treating male infertility of the present invention is to be administered to male of mammals, and examples of mammals include human, cattle, swine, sheep, goat, mouse, rat, rabbit, dog and cat.

Preferred levels of the therapeutic effect of the agent for treating male infertility of the present invention can be suitably exemplified by a conception rate of 85% or more in the copulated animals in the experiment of Example 2 described in the following. A conception rate of 90% or more can be more preferably exemplified, and 94% or more can be further preferably exemplified.

Further, a preferred level in a different embodiment can be exemplified by a sperm motility on day 21 after the administration of the agent of the present invention which is 1.5-fold or more of that of before the administration (day 0), in the experiment described in Example 4 in the following. A motility of 2.0-fold or more can be more preferably exemplified, a motility of 3-fold or more motility can be further preferably exemplified, and a motility of 4-fold or more can be further more preferably exemplified. Further, it can be preferably exemplified by a sperm survival rate (%) on day 21 after the administration of the agent of the present invention which is 1.2-fold or more relative to that of before the administration (day 0). A survival rate of 1.5-fold or more can be more preferably exemplified, and a survival rate of 1.8-fold or more can be further suitably exemplified, and a survival rate of 2.1-fold or more can be further more preferably exemplified.

Further, the present invention encompasses use of δ-amino levulinic acid, its derivative, or salt thereof and an iron compound in the manufacture of an agent for treating male infertility, use of δ-amino levulinic acid, its derivative, or salt thereof and an iron compound for treating male infertility, and a method for treating male infertility comprising administering δ-amino levulinic acid, its derivative, or salt thereof and an iron compound to mammals (particularly human).

EXAMPLES

In the following, the present invention will be explained further by referring to the Examples, while the present invention is not limited to these.

Example 1

Forty 10 week-old male rats (Slc:Wistar) and forty 9 week-old female rats were obtained, quarantined for 7 days, and were habituated and bred for 13 days. δ-amino levulinic acid (herein after referred to as ALA) phosphate was weighed, dissolved into injection solvent to prepare a 50 mg/mL solution. The solution was administered orally once a day continuously to twenty 12 week-old male rats for 14 days before crossing, and for 49 to 52 days after crossing until the day before autopsy, by using a sonde for oral administration for rats at a dose of 500 mg/kg (500 mg/kg-group). To the control group, the solution was administered similarly by using an injection solvent to twenty 12 week-old male rats. By making the first day of administration as day 1, the general state, body weight, ingested amount, autopsy (weight of the testis, epididymis, seminal vesicle (including coagulating gland) and prostate gland) were observed and measured.

As a result, as it is shown in FIG. 1, concerning the net weight and the weight volume ratio to the body weight of seminal vesicle, the 500 mg/kg-group showed a significant high level compared to the control group. No significant difference was observed for right and left testis, right and left epididymis, and prostate gland.

Example 2

After day 15 from administration of Example 1, crossing period was set as 14 days, and 1 female was housed per 1 male in the control group and in the 500 mg/kg-group.

As a result, the conception rate of copulated animals was 80.0% in the control group (conception succeeded for 16 out of 20 rats), while it was as high as 94.4% in the 500 mg/kg-group (conception succeeded for 17 out of 19 rats; 1 rat died by biting the sonde for oral administration).

Example 3

1 g of ALA hydrochloride was dissolved into 50 mL of 5% glucose aqueous solution (test solution), and administered to 7 healthy volunteers, married men from 28 to 44 years old. They ingested orally the test solution (13.9 to 22.2 mg/kg) without taking breakfast. Estimation was made according to their individual subjective estimation: Specifically, by using their individual sexual experience as a standard; when erectile promoting sexual intercourse was observed, it was denoted by (○), when no change is observed by (Δ), and when the situation was engraved by (x).

As a result, as it is shown in Table 1, erectile was observed for 5 out of 7 on that night, among which 2 had sexual intercourse, and pregnancy was confirmed.

TABLE 1

| Volunteer | Age | Body weight (kg) | Dosage (mg/kg) | Result | Note |
|---|---|---|---|---|---|
| 1 | 43 | 68 | 14.7 | ○ | No sexual intercourse, |
| 2 | 34 | 58 | 17.2 | ○ | sexual intercourse: pregnant |
| 3 | 37 | 60 | 16.7 | ○ | sexual intercourse pregnant |
| 4 | 28 | 55 | 18.2 | Δ | No sexual intercourse |
| 5 | 49 | 72 | 13.9 | ○ | No sexual intercourse |
| 6 | 38 | 45 | 22.2 | Δ | No sexual intercourse |
| 7 | 55 | 63 | 15.9 | ○ | No sexual intercourse |

From the above, it was confirmed that ALA was useful as an agent for treating male infertility.

Example 4

In order to confirm whether the agent for treating male infertility of the present invention ameliorates actually sperm motility and survival rate, the following experiment was conducted by using a dog as a test animal.

The dog was a male miniature poodle of age 7, born on Jan. 28, 2001. Its body weight was 2.55 kg when starting the administration of ALA. A mixture of ALA phosphate and sodium ferrous citrate (ALA phosphate: sodium ferrous citrate=1:4 (molar ratio) was prepared as a formulation for administering to this male dog. This formulation was administered orally to this male dog once a day for 21 consecutive days from Nov. 27, 2008, at a dose of 3.33 mg/day in terms of ALA phosphate. Sperms were collected 3 times from the dog, just before the administration of the formulation (day 0), on day 8, and on day 21 after the administration. Sperms just after collection were observed with a microscope, and the vitality was evaluated on a 5-point scale. Further, sperm motility and survival rate (%) were calculated from the vitality test results.

Evaluation standard for evaluating the vitality and the evaluation results are shown in the following Table 2.

TABLE 2

| | Evaluation standard | Day 0 | Day 8 | Day 21 |
|---|---|---|---|---|
| +++ | Spiral active forward progression | 0 | 0 | 20 |
| ++ | Active forward progression | 10 | 5 | 50 |
| + | Slow forward progression | 10 | 0 | 10 |
| ± | Fixed-position motion | 20 | 90 | 10 |
| – | arrested | 60 | 5 | 10 |

The motility was calculated by setting "+++" as 100, "++" as 75, "+" as 50, "±" as 25 and "–" as 0, and by using these evaluation values and the ratio of each evaluation level to the evaluation results in the Table 2. For example, the motility on day 0 was calculated by 100×0+75×10+50×10+25×20+0×60, and by rounding the fractional part to obtain 18. The survival rate (%) was calculated by determining the evaluation standard "–" as dead sperm, and for other than "–" as living sperm. The motility and survival rate (%) calculated for the collected sperms are shown in Table 3.

TABLE 3

| | Day 0 | Day 8 | Day 21 |
|---|---|---|---|
| Motility | 18 | 28 | 75 |
| Survival rate (%) | 40 | 95 | 90 |

As it is shown from the results of Table 3, by administrating the formulation of the present invention, both sperm motility and survival rate (%) of the test animal (dog) were improved. From these results, it was shown that the formulation of the present invention has a therapeutic effect for oligozoospermia and asthenospermia.

INDUSTRIAL APPLICABILITY

The present invention can be used in the field of treatment of male infertility.

The invention claimed is:

1. A method of treating male infertility in a patient in need thereof comprising administering 6-amino levulinic acid shown by general formula (I), its derivative or salt thereof as an active ingredient, $$R^2R^1NCH_2COCH_2CH_2COR^3 \quad (1)$$

wherein $R^1$ and $R^2$ independently represent a hydrogen atom, alkyl group, acyl group, alkoxycarbonyl group, aryl group, or aralkyl group; $R^3$ represents a hydroxy group, alkoxy group, acyloxygroup, alkoxycarbonyloxy group, aryloxy group, aralkyloxy group or amino group, to the patient in need thereof, wherein the male infertility is caused by oligozoospermia or asthenospermia.

2. The method of claim 1, further comprising an iron compound as an active ingredient.

3. The method of claim 2, wherein the iron compound is 1 or more compound(s) selected from ferric chloride, iron sesquioxide, sodium iron chlorophyllin, ferritin iron, ferrous citrate, iron sodium citrate, iron ammonium citrate, ferrous fumarate, ferrous pyrophosphate, ferric pyrophosphate, saccharated iron oxide, iron acetate, iron oxalate, ferrous succinate, iron sodium succinate citrate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate.

4. The method of claims 1 to 3, wherein δ-amino levulinic acid, or salt thereof is administered in an amount of 0.001 mg to 10 g per 1 kg of body weight at one time.

5. The method of claim 2 or 3, wherein the iron compound is administered in an amount of 0.001 mg to 10 g per 1 kg of body weight at one time.

6. The method of claims 1 to 3, wherein the administration method is oral administration, intraperitoneal administration, intravenous administration, intramuscular administration, local administration to affected area, transdermal administration, or intrarectal administration.

* * * * *